United States Patent
McCormack et al.

[11] Patent Number: 5,997,981
[45] Date of Patent: Dec. 7, 1999

[54] BREATHABLE BARRIER COMPOSITE USEFUL AS AN IDEAL LOOP FASTENER COMPONENT

[75] Inventors: Ann Louise McCormack, Cumming; William Bela Haffner, Kennesaw; Wanda Walton Jackson, Alpharetta, all of Ga.

[73] Assignee: Kimberly-Clark Worldwide, Inc., Neenah, Wis.

[21] Appl. No.: 08/929,432

[22] Filed: Sep. 15, 1997

[51] Int. Cl.$^6$ .................................................. B32B 3/06
[52] U.S. Cl. ........................... 428/99; 24/306; 24/444; 24/448; 24/451; 428/100; 428/516; 442/394; 604/370; 604/384
[58] Field of Search ............... 428/99, 100, 516; 604/370, 384; 442/394; 24/306, 448, 451, 444

[56] References Cited

U.S. PATENT DOCUMENTS

| | | | |
|---|---|---|---|
| D. 239,566 | 4/1976 | Vogt | D59/2 R |
| D. 356,688 | 3/1995 | Uitenbroek et al. | D5/52 |
| 3,692,618 | 9/1972 | Dorschner et al. | 161/72 |
| 3,802,817 | 4/1974 | Matsuki et al. | 425/66 |
| 3,855,046 | 12/1974 | Hansen et al. | 161/150 |
| 4,340,563 | 7/1982 | Appel et al. | 264/518 |
| 4,600,618 | 7/1986 | Raychok, Jr. et al. | 428/92 |
| 4,761,318 | 8/1988 | Ott et al. | 428/85 |
| 5,032,122 | 7/1991 | Noel et al. | 604/391 |
| 5,300,365 | 4/1994 | Ogale | 428/461 |
| 5,326,612 | 7/1994 | Goulait | 428/100 |
| 5,354,591 | 10/1994 | Ott et al. | 428/99 |
| 5,382,462 | 1/1995 | Pacione | 428/95 |
| 5,407,439 | 4/1995 | Goulait | 604/391 |
| 5,476,702 | 12/1995 | Datta et al. | 428/99 |
| 5,498,461 | 3/1996 | Rockney | 428/100 |
| 5,539,056 | 7/1996 | Yang et al. | 525/240 |
| 5,569,233 | 10/1996 | Goulait | 604/391 |
| 5,595,567 | 1/1997 | King et al. | 604/391 |
| 5,596,052 | 1/1997 | Resconi et al. | 526/127 |
| 5,614,281 | 3/1997 | Jackson et al. | 428/100 |
| 5,616,394 | 4/1997 | Gorman et al. | 428/99 |
| 5,647,864 | 7/1997 | Allen et al. | 604/391 |
| 5,695,868 | 12/1997 | McCormack | 428/516 |
| 5,855,999 | 1/1999 | McCormack | 428/516 |

FOREIGN PATENT DOCUMENTS

| | | |
|---|---|---|
| 34 03 258 | 8/1985 | Germany. |
| 35 20 630 | 12/1986 | Germany. |
| 86 03164 | 6/1986 | WIPO. |
| 92/20251 | 11/1992 | WIPO. |
| 97/24482 | 7/1997 | WIPO. |

OTHER PUBLICATIONS

Case No. 13257, patent application entitled "Breathable Filled Film Laminate" filed Sep. 15, 1997.
Case No. 13324, patent application entitled "Nonwoven Bonding Patterns Producing Fabrics with Improved Strength and Abrasion Resistance" filed Sep. 15, 1997.
Serial No. 773,826 patent application filed Dec. 27, 1996 entitled "Stable and Breathable Films of Improved Toughness and Method of Making the Same." This was abandoned on Aug. 11, 1997 replaced by Serial No. 08/853,025 filed May 8, 1997, same title.

*Primary Examiner*—Nasser Ahmad
*Attorney, Agent, or Firm*—William D. Herrick

[57] ABSTRACT

A composite material adapted for mechanical fastener use as a loop fastener component with a complementary hook component is made by laminating a film with an amorphous polymer layer to a prebonded nonwoven web under conditions producing laminate bonds corresponding to the prebond locations, and loose filaments or fibers between the bonds. The composite also desirably has a MVTR of at least about 100 g/m$^2$/24 hours and a hydrohead of at least about 50 mbar. In use as a component of a disposable personal care product such as a disposable diaper, the loop fastener component may be substantially the entire backing, providing comfort, protection and highly variable fit.

18 Claims, 5 Drawing Sheets

BREATHABLE BARRIER COMPOSITE USEFUL AS AN IDEAL LOOP FASTENER COMPONENT

BACKGROUND OF THE INVENTION

1. Field of the Invention

The present invention relates to composite materials having breathable barrier applications and particularly useful as a component of fasteners of the hook and loop type typified by those extensively marketed by VELCRO INTERNATIONAL and now available from numerous sources for applications from shoe ties to golf gloves and many others where nonpermanent attachment is desired. These fasteners fundamentally include a hook member and a loop member that, when pressed together, entangle in a manner that resists shear forces but can be separated when subjected to a desired level of peel force. The design of these members has become quite sophisticated and provides a wide range of properties obtainable by varying factors such as hook shape, size and flexibility as well as similar loop features. For many low cost applications such as fasteners for disposable garment applications like diapers and adult incontinent wear, it has been necessary to develop inexpensive manufacturing techniques and materials for such fasteners that, nevertheless, meet the performance requirements. Particularly for such applications where the loop component also serves as the backing material, it is highly desirable that it be both breathable for comfort and serve as a barrier to prevent leakage. The present invention provides an ideal loop fastener component particularly suited to such disposable product applications.

2. Background

The art is replete with references to hook and loop type fasteners and components for such fasteners intended for use in disposable product applications such as disposable diapers and the like. Just by way of example, reference may be had to coassigned U.S. Pat. No. 5,614,281 to Jackson et al. which, itself, provides much background information and for that purpose is incorporated herein by reference in its entirety. Other loop fastener materials are described in, for example, U.S. Pat. No. 4,761,318 to Ott et al., U.S. Pat. No. 5,032,122 to Noel et al., U.S. Pat. No. 5,326,612 to Goulait, U.S. Pat. No. 5,595,567 to King et al, and U.S. Pat. No. 5,647,864 to Allen et al. Briefly, a particularly economical loop component may be formed using nonwoven manufacturing techniques such as spunbonded processes that result in significant areas of the web between bond points where the filaments are unbonded to each other and available to engage hooks of a complementary hook member. Factors, such as configuration, number and area coverage of the bonds in the nonwoven as well as the selection of a particular hook member, may be varied to achieve a desired level of peel strength and other properties within a designated cost range. In addition, the selection of a polymer or other compositional ingredient for the nonwoven and/or the hook component can affect the performance and/or cost of the fastener in a given application. There remains a need for a loop fastener component that can have tailored properties such as peel strength, shear strength and refastenability as well as breathable barrier functions at a cost consistent with use as a backing component of disposable products. Other uses for breathable barrier materials having clothlike attributes such as surgical gowns and drapes, for example, will be apparent to those skilled in the art.

SUMMARY OF THE INVENTION

The present invention is directed to a breathable barrier nonwoven composite material particularly adapted for use as a loop fastener component that includes a laminate of a film layer and a prebonded nonwoven layer wherein the laminate bonds occur at the bond sites of the prebonded nonwoven, leaving filaments or fibers between such bond sites unbonded. For improved comfort and utility as a backing component of a personal care product such as a disposable diaper, for example, the laminate is breathable with a moisture vapor transmission rate above about 100 $g/m^2/24$ hours and has a hydrohead value of at least 50 mbar of water. In use with a complementary hook component a loop fastener formed from this composite provides capability for fastening anywhere on the backing of the product and consistent refastenability over a period of time and for the number of cycles of opening and closing that is suitable for many disposable and limited use applications. The nonwoven layer contains a bond pattern of either uniform or nonuniform bond impressions that result in an unbonded area of at least 70%, taken over any 100 cm square of nonwoven surface. In addition the bond frequency provides a pattern density in the range of from about 50 to about 200 bonds/in.$^2$ with an area coverage of from about 5% to about 30%, advantageously from about 10% to about 25%. The film layer is either a multilayer or coextruded structure with an exposed layer of a soft, amorphous polymer, or a monolayer and, in either case, is a predominantly microporous liquid barrier that is conformable and compatible with the nonwoven. Lamination may be achieved by an application of heat and pressure taking advantage of the amorphous polymer properties either in the multilayer film, or as the separately applied bonding layer in the monolayer film embodiment, for example. To enhance clothlike aesthetics and engagement of hook elements for the loop component applications, a retracted laminate may be formed by stretching the film prior to lamination to the nonwoven and subsequently allowing the laminate to relax or retract, producing a textured surface of loops formed by unbonded inter-bond filaments or fibers between bond areas where the film and nonwoven remain securely attached. The invention also includes the method for making the loop fastener component.

DETAILED DESCRIPTION

Definitions

As used herein the following terms have the specified meanings, unless the context demands a different meaning, or a different meaning is expressed; also, the singular generally includes the plural, and the plural generally includes the singular unless otherwise indicated.

"Nonwoven" means a web of fibers or filaments that is formed by means other than knitting or weaving and that contains bonds between some or all of the fibers or filaments; such bonds may be formed, for example, by thermal, adhesive or mechanical means such as entanglement.

"Fiber" means an elongated strand of defined length, such as staple fibers formed by cutting a continuous strand into lengths of, for example, 2 to 5 cm. Collections of fibers may have the same or different lengths.

"Filament" means a generally continuous strand that has a very large ratio of length to diameter, for example, 1000 or more.

"Spunbond" means a nonwoven of filaments formed by melt extrusion of a polymer into strands that are quenched and drawn, usually by high velocity air, to strengthen the filaments which are collected on a forming surface and bonded, often by the patterned application of heat and pressure. Spunbonded processes are described, for example, in the following patents to which reference may be made for additional details: U.S. Pat. No. 4,340,563 to Appel et al., U.S. Pat. No. 3,802,817 to Matsuki et al., and U.S. Pat. No. 3,692,618 to Dorschner et al.

"Loop" means an area of separation of at least one fiber or filament from others in a nonwoven and includes but is not limited to configurations where the same fiber or filament intersects itself; i.e. a complete circle or oval, for example, need not be formed.

"Complementary hook" means a structure adapted for use as a mechanical fastener component and having projections of a profile, height, density, geometry and orientation so as to releasably attach to a loop fastener material of the invention and provide the intended level of hook peel and shear strength properties. The projections need not form a "hook" but may have other configurations such as a mushroom shape, for example. Suitable hook materials may be unidirectional or bidirectional, for example, and often comprise from about 16 to about 620 hooks per square centimeter and hook heights of from about 0.00254 cm to about 0.19 cm. They are available, for example, from Velcro International of Manchester, N.H. and 3M of St. Paul, Minn.

"Amorphous Polymer" when used herein to describe a bonding layer either as a multilayer film component or separately applied layer means a thermoplastic polymer such as certain polyolefins with a density in the range of from about 0.85 to about 0.89 and low crystallinity, for example, less than about 30% such as those frequently used as components of adhesives and having limited hot melt properties.

"Thermal point bonding" involves passing a fabric or web of fibers to be bonded between a heated calender roll and an anvil roll. The calender roll is patterned in some way so that the entire fabric is not bonded across its entire surface. As a result, many patterns for calender rolls have been developed for functional as well as aesthetic reasons. As will be understood by those skilled in the art, bond area percentages are, of necessity, described in approximations or ranges since bond pins are normally tapered and wear down over time. As those skilled in the art will also recognize, references to "pins/in.$^2$" and "bonds/in.$^2$" are somewhat interchangeable since the anvil pins will create bonds in the substrate in essentially the same sizes and surface relationship as the pins on the anvil. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin may have a side dimension of 0.038 inches (0.965 mm), for example, resulting in a pattern having a bonded area of about 30%. Another typical point bonding pattern is the expanded Hansen and Pennings or "EHP" bond pattern which produces a bond area of about 15% to 18% which may have a square pin having a side dimension of 0.037 inches (0.94 mm), for example, and a pin density of about 100 pins/in$^2$. Another typical point bonding pattern designated "714" has square pin bonding areas wherein each pin may have a side dimension of 0.023 inches, for example, for a bond area of 15% to 20% and about 270 pins/in$^2$. Other common patterns include a "Ramisch" diamond pattern with repeating diamonds having a bond area of 8% to 14% and 52 pins/in.$^2$ as well as a wire weave pattern looking as the name suggests, e.g. like a window screen and having a bond area of 15% to 20% and 302 bonds/in.$^2$. Typically, the percent bonding area varies widely from around 10% to around 30% of the area of the fabric laminate web and the number of pins/in$^2$ also may vary over a wide range. Of the practically limitless combinations of bond configurations, however, only selected bond patterns are useful in accordance with the invention. These will have a bond area in the range of from about 5% to about 30%, desirably in the range of from about 10% to about 25% and a bond frequency in the range of from about 50 to about 200 per square inch, desirably in the range of from about 75 to about 125 per square inch. When used herein, the term "prebonded" nonwoven means those nonwovens having been bonded with a pattern defined as useful in accordance with these parameters. As is well known in the art, the spot bonding holds the laminate layers together as well as imparts integrity to each individual layer by bonding filaments and/or fibers within each layer.

Test Procedures

Hydrohead: A measure of the liquid barrier properties of a fabric is the hydrohead test. The hydrohead test determines the height of water (in mbars) which the fabric will support before a predetermined amount of liquid passes through. A higher hydrohead reading indicates that a fabric is a better barrier to liquid penetration than a fabric with a lower hydrohead. The hydrohead test is performed according to Federal Test Standard 191A, Method 5514.

Grab Tensile test: The grab tensile test is a measure of breaking strength and elongation or strain of a fabric when it is subjected to unidirectional stress. This test is known in the art and conforms to the specifications of Method 5100 of the Federal Test Methods Standard 191A. The results are expressed in pounds or grams to break and percent stretch before breakage. Higher numbers indicate a stronger, more stretchable fabric. The term "load" means the maximum load or force, expressed in units of weight, required to break or rupture the specimen in a tensile test. The term "total energy" means that total energy under a curve of load versus elongation, as expressed in weight-length units. The term "elongation" means the increase in length of a specimen during a tensile test. The grab tensile test uses two clamps, each having two jaws with each jaw having a facing in contact with the sample. The clamps hold the material in the same plane, usually vertically, separated by 3 inches (76 mm) and move apart at a specified rate of extension. Values for grab tensile strength and grab elongation are obtained using a sample size of 4 inches (102 mm) by 6 inches (152 mm), with a jaw facing size of 1 inch (25 mm) by 1 inch, and a constant rate of extension of 300 mm/min. The sample is wider than the clamp jaws to give results representative of effective strength of fibers in the clamped width combined with additional strength contributed by adjacent fibers in the fabric. The specimen is clamped in, for example, a Sintech 2 tester, available from the Sintech Corporation, 1001 Sheldon Dr., Cary, N.C. 27513, an Instron Model TM, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154. This closely simulates fabric stress conditions in actual use. Reported results are the average of three specimens tested and may be performed with the specimens in the cross direction (CD) or in the machine direction (MD).

Strip Tensile: The strip tensile test is similar to the grab tensile and measures the peak and breaking loads and peak and break percent elongations of a fabric. This test measures the load (strength) in grams and elongation in percent. In the strip tensile test, two clamps, each having two jaws with each jaw having a facing in contact with the sample, hold the material in the same plane, usually vertically, separated by 3 inches and move apart at a specified rate of extension. Values for strip tensile strength and strip elongation are obtained using a sample size of 3 inches by 6 inches, with a jaw facing size of 1 inch high by 3 inches wide, and a constant rate of extension of 300 mm/min. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154 may be used for this test. Reported results are the average of three specimens tested and the test may be performed with the specimen in the cross direction (CD) or in the machine direction (MD).

Peel test: In peel or delamination testing a laminate is tested for the amount of tensile force which will pull the layers of the laminate apart. Values for peel strength are obtained using a specified width of fabric, clamp jaw width and a constant rate of extension. For samples having a film side, the film side of the specimen is covered with masking tape, or some other suitable material, in order to prevent the film from ripping apart during the test. The masking tape is on only one side of the laminate and so does not contribute to the peel strength of the sample. This test uses two clamps, each having two jaws with each jaw having a facing in contact with the sample, to hold the material in the same plane, usually vertically, separated by 2 inches to start. The sample size is 4 inches wide by as much length as necessary to delaminate enough sample length. The jaw facing size is 1 inch high by at least 4 inches wide, and the constant rate of extension is 300 mm/min. The sample is delaminated by hand a sufficient amount to allow it to be clamped into position, and the clamps move apart at the specified rate of extension to pull the laminate apart. The sample specimen is pulled apart at 180° of separation between the two layers, and the peel strength reported is an average of three tests, peak load in grams. Measurement of the force begins when 16 mm of the laminate has been pulled apart, and it continues until a total of 170 mm has been delaminated. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or the Thwing-Albert Model INTELLECT II available from the Thwing-Albert Instrument Co., 10960 Dutton Rd., Phila., Pa. 19154, may be used for this test. The test may be performed with the specimen in the cross direction (CD) or in the machine direction (MD).

Martindale Abrasion test: This test measures the relative resistance to abrasion of a fabric. The test results are reported on a scale of 1 to 5, with 5 being the least wear and 1 the most, after 120 cydes with a weight of 1.3 pounds per square inch. The test is carried out with a Martindale Wear and Abrasion Tester such as model no. 103 or model no. 403 available from James H. Heal & Company, Ltd. of West Yorkshire, England. The abradant used is a 36 inch by 4 inch by 0.05 thick silicone rubber wheel reinforced with fiber glass having a rubber surface hardness 81A Durometer, Shore A of 81 plus or minus 9. The abradant is available from Flight Insulation Inc., a distributor for Connecticut Hard Rubber, 925 Industrial Park, NE, Marietta, Ga. 30065.

Basis Weight: the basis weights of various materials described herein were determined in accordance with Federal Test Method No. 191A/5041. Sample size for the sample materials was 15.24×15.24 centimeters, and three values were obtained for each material and then averaged. The values reported below are the averages.

Hook Peel: the 180° peel strength test is intended to measure how well hook and loop components engage, and it involves attaching a hook material to a loop material of a hook and loop fastening system, and then peeling the hook material from the loop material at a 180° angle. The maximum load is recorded in grams as an average of the three highest peak load values needed to disengage or peel the two materials. To perform the test, a continuous rate of extension tensile tester with a 5000 gram full scale load is required, such as a Sintech System 2 Computer Integrated Testing System available from Sintech, Inc., having offices in Research Triangle Park, N.C. A 3 inch (7.6 cm) by 6 inch (15.2 cm) sample of the loop material is used. A 2.5 inch (6.3 cm) wide sample of hook material, which is adhesively and ultrasonically secured to a substantially inelastic, nonwoven material, is positioned hook side down over and applied to the upper surface to cover the loop material sample with about a one inch overlap. To ensure adequate and uniform engagement of the hook material to the loop material, a wringer, Model LW 1, part number 14-9969 from Atlas Electric Devices Co., Chicago, Ill. is used to squeeze the combined hook and loop materials for one cycle, with one cycle equaling a pass through the wringer using a total of 40 pounds weight. One end of the fingertab material supporting the hook material is secured within the upper jaw of the tensile tester, while the end of the loop material directed toward the upper jaw is folded downward and secured within the lower jaw of the tensile tester. The placement of the respective materials within the jaws of the tensile tester should be adjusted such that minimal slack exists in the respective materials and the gage length is 3 inches (7.6 cm) prior to activation of the tensile tester. The hook elements of the hook material are oriented in a direction generally perpendicular to the intended directions of movement of the tensile tester jaws. The tensile tester is activated at a constant rate of separation of 500 mm per minute and the peak load in grams to disengage or peel the hook material from the loop material at a 180° angle is then recorded, based on the average of the three highest peaks.

Hook Shear: the dynamic shear strength test involves engaging a hook material to a loop material of a hook and loop fastening system and then pulling the hook material across the loop material's surface. The maximum load required to disengage the hook from the loop is measured in grams. To conduct this test, a constant rate of extension tensile tester with a 5000 gram full scale load is required, such as Sintech System 2 Computer Integrated Testing System. A 3 inch by 6 inch sample of the loop material is attached with masking tape to a flat support surface and then cut in half in the shorter direction. A sample of hook material 2.5 in.×0.75 in., which is adhesively and ultrasonically secured to a substantially inelastic, nonwoven material, is positioned over and applied to the upper surface of the loop material sample centered in the shorter direction and 2 inches in from the cut edge. To ensure adequate and uniform engagement of the hook material to the loop material, a wringer, Model LW 1, part number 14-9969 from Atlas Electric Devices Co., Chicago, Ill. is used to squeeze the combined hook and loop materials for one cycle, with one cycle equaling a MD (longer dimension) pass, through the wringer using a total of 40 pounds weight. One end of the nonwoven material supporting the hook material is secured within the upper jaw of the tensile tester, and the end of the loop material directed toward the lower jaw is secured within the lower jaw of the tensile tester. The placement of the respective materials within the jaws of the tensile tester should be adjusted such that minimal slack exists in the respective materials prior to activation of the tensile tester. The hook elements of the hook material are oriented in a direction generally perpendicular to the intended directions of movement of the tensile tester jaws. The tensile tester is activated at a gage length of 3 inches and crosshead speed of 250 mm per minute and the peak load to disengage the hook material from the loop material is then recorded in grams as the average of the highest peaks for three specimens.

DETAILED EMBODIMENTS

The invention will be described with reference to the drawings and examples which illustrate certain embodiments. It will be apparent to those skilled in the art that these embodiments do not represent the full scope of the invention which is broadly applicable in the form of variations and equivalents as may be embraced by the claims appended hereto. It is intended that the scope of the claims extend to all such variations and equivalents.

Figure 1:
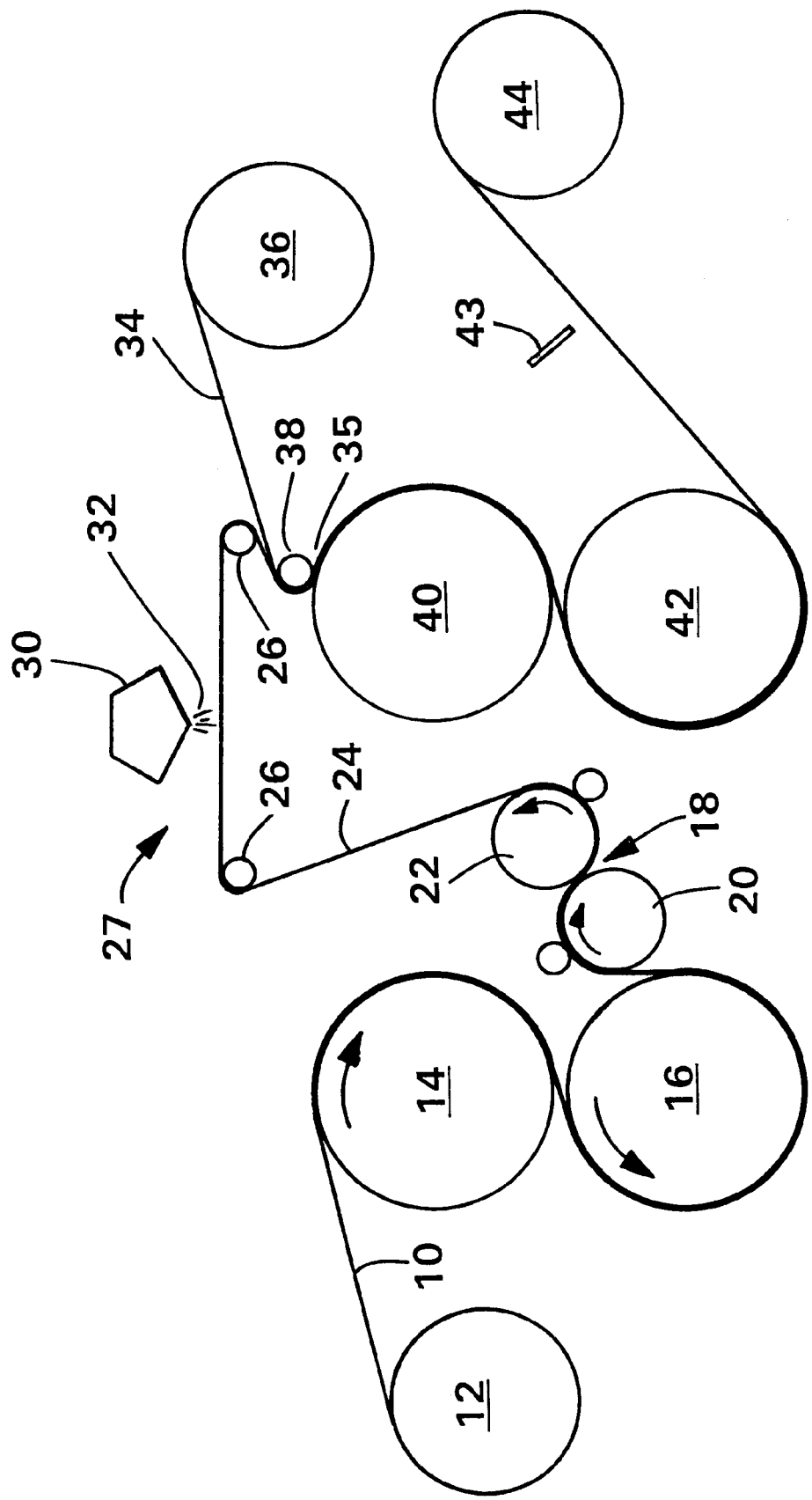
FIG. 1 is a schematic illustration of a process for making the loop fastener material of the present invention.

Referring to FIG. 1, the illustrated process begins with a filled film 10 that is unwound from roll 12 and preheated, for example, by contact with heated rotating drums 14, 16. The temperature to which the film 10 is heated will depend on the composition of the film as well as the breathability and other desired end properties of the composite material. For example, as a loop fastener, the amount of retraction will affect the size of loops. In most cases the film will be heated to a temperature no higher than 10° C. below its melting point. The purpose for heating the film is to allow it to be stretched quickly without causing film defects. The heated film is stretched in the machine direction in a machine direction orientor section 18 comprising rotating rolls 20, 22 and associated pressure rolls. Roll 22 is driven faster than roll 20 with the result that the film is stretched in the direction of travel ("machine direction" or "MD"). The amount of stretching will depend on the desired end properties of the loop fastener, but, in general, the film will be stretched to at least about 300% of its original length but less than the amount that tends to result in film defects. For most applications with films based on polyolefins, for example, the stretch will be to at least 200% of the original film length and, frequently, in the range of about 250% to 500%. Stretched film 24 is carried over support rolls 26, 28 through an optional bonding station 27 where applicator 30 applies an amorphous polymer, for example, polyolefin resin 32 if desired. As will be explained in detail below, amorphous polymer application is not necessary for certain embodiments of the invention where it is a film component layer, and, in those cases, this station may be eliminated and the laminate thermally bonded at nip 35. A facing layer 34 of a prebonded nonwoven is unwound from roll 36 and combined with stretched film 24 in front of pressure roll 38. After nip 35, the two layers are allowed to relax, with or without heating, and the laminate is wound at a reduced speed, for example, 80% to 90% of the nip speed passing over rotating roll 40 which is driven at a speed that permits film 24 to retract to cause puckering of facing layer 34. After roll 40 the combined layers are annealed by contact with heated roll 42 which is driven at about the speed of roll 40 to avoid significant additional stretching. The annealing temperature will vary according to the desired end properties of the loop fastener material and the composition of the layers, but may be, for example, within 15° C. of the temperature used in stretching. After annealing, the combined layers may be cooled, for example, by contact with air from air knife 43 or chill rolls, if desired, or collected directly as roll 44 or directed to a converting line for incorporation into a personal care product. While not shown, an embossing step may be used, if desired, to impart an attractive pattern to the composite by, for example, passing it between embossing rolls in a manner well known to those skilled in this art.

As will be apparent to those skilled in the art, the above process is adaptable to many films and facing layers to produce breathable barrier loop fastener material having widely varying properties. To work effectively as a loop fastener material in accordance with the invention, however, selection of these components desirably takes into consideration a number of factors. The film, for example at the low weights, must be robust enough to withstand the process steps necessary to provide desired flexibility and softness as well as to maintain low cost. In addition, the film must be capable of bonding effectively to the facing layer and maintaining barrier properties and moisture vapor transmission rates. For many applications it will be desired that the stretched film provide opacity to the composite as well.

Films meeting these requirements include polymers, such as polyethylene, polypropylene, blends including polyolefins and copolymers such as ethylene and propylene copolymers, for example generally having a basis weight in the range of from about 10 gsm to about 50 gsm, advantageously for loop component applications, in the range of from about 15 gsm to about 30 gsm. Specific examples include linear low density polyethylenes such as Dowlexe 2535, 3347 and 3310, Affinity® 5200 available from Dow Chemical Company of Midland, Michigan. The film compositions desirably contain up to about 40% by weight of a filler such as calcium carbonate and especially about 45% to about 65% by weight of such filler. Examples include Supercoate calcium carbonate from English China Clay of Sylacauga, Ala. which contains a coating of about 1.5% by weight of either stearic acid or behenic acid to enhance dispersion of the filler. Particularly advantageous film examples include coextruded films having on one or both sides a thin, external layer of an amorphous polymer such as a propene-rich polyalphaolefin terpolymer or copolymer which allows bonding to the facing layer without requiring a separately applied bonding layer. An example is Catalloy polymer from Montell USA, Inc. of Wilmington, Del. which is an olefinic multistep reactor product wherein an amorphous ethylene propylene random copolymer is molecularly dispersed in a predominantly semicrystalline high propylene monomer/low ethylene monomer continuous matrix, an example of which is described in U.S. Pat. No. 5,300,365 to Ogale. In addition, the amorphous polymer layer may also include hot melt adhesives or other amorphous polyalphaolefin resins, which desirably have a melt viscosity of 100,000 mPa sec or greater, in an amount of, for example, up to about 50% by weight of the polymer fraction, so long as the above described breathable barrier properties are retained. Commercially available amorphous polyalphaolefins, such as those used in hot melt adhesives, are suitable for use with the present invention and include, but are not limited to, REXTAC® ethylenepropylene APAO E-4 and E-5 and butylene-propylene BM-4 and BH-5, and REXTAC® 2301 from Rexene Corporation of Odessa, Tex., and VESTOPLAST® 792 from Huls AG of Marl, Germany. These amorphous polyolefins are commonly synthesized on a Ziegler-Natta supported catalyst and an alkyl aluminum co-catalyst, and the olefin, such as propylene, is polymerized in combination with varied amounts of ethylene, 1-butene, 1-hexane or other materials to produce a predominantly atactic hydrocarbon chain. Also useful are certain elastomeric polypropylenes such as are described, for example, in U.S. Pat. No. 5,539,056 to Yang et al. and U.S. Pat. No. 5,596,052 to Resconi et al., incorporated herein by reference in their entireties, and polyethylenes such as AFFINITY®, EG 8200, from Dow Chemical of Midland, Mich. as well as EXACT® 4049, 4011 and 4041 from Exxon of Houston, Tex., as well as blends including one or more tackifiers and KRATON® from Shell Chemical Company of Houston, Tex. A composite with the bonding layer on one side only may have the advantage of a higher moisture vapor transmission rate if desired. Such films are described in greater detail in coassigned US patent application Ser. No. 929,562 (Attorney Docket No. 13257) filed on even date herewith in the names of McCormack and Haffner and entitled "Breathable Filled Film Laminate" (Express Mailing No. RB 879 662 575 US) the contents of which are incorporated herein in their entirety by reference. Other film layers will be apparent to those skilled in the art in light of the examples provided herein.

The prebonded facing layer will be selected so as to be compatible with the film or bonding layer and will have properties such as basis weight, bulk, and strength adequate for the intended use. Primarily for economic reasons, nonwoven webs are preferred, especially spunbonded nonwovens having a basis weight generally in the range of from about 10 gsm to about 50 gsm, for example, frequently within the range of from about 15 gsm to about 25 gsm. The composition of the facing layer will be selected to be compatible with the film layer while providing the desired properties in the loop fastener component. Generally useful are synthetic polymers such as polyolefins, for example, polypropylene, polyethylene, blends and copolymers including propylene and ethylene. Such nonwovens are described above and in the references provided herein, and their manufacture is known to those skilled in this art. Specific examples include ACCORD® spunbond nonwovens available from Kimberly-Clark Corporation, Dallas, Tex. The bond pattern, for the facing layer, as mentioned above, will provide for looping between bonds to provide attachment areas for complementary hooks. Useful examples include an expanded RHT pattern as illustrated in U.S. Design Pat. No. 239,566 to Vogt, an EHP pattern, a Delta Dot pattern which comprises rows of offset circular bonds having about 102 pins/in.$^2$ for a bond area of 9% to 20%, and a Ramish pattern as above described. One advantageous bond pattern for a spunbond facing web is a "S" weave pattern as described in coassigned, contemporaneously filed U.S. patent application Ser. No. 929,808 (Attorney Docket No. 13,324) in the names of McCormack, Fuqua, and Smith, and entitled "Nonwoven Bonding Patterns Producing Fabrics with Improved Strength and Abrasion Resistance" (Express Mailing No. EM 331 625 424 U.S.) which is incorporated herein by reference in its entirety. In all cases the % bond area will be less than about 30% and bond density from about 50 to about 200/in.$^2$. In addition, for the application for the loop fastener component, the facing will desirably have a tensile strength measured as described above, of at least about 3000 g taken in the machine direction, and at least about 1500 g taken in the cross-machine direction, and advantageously a Martindale abrasion, measured as described above, of at least about 3.

When used, the separately applied amorphous polymer bonding layer will be compatible with both facing and film layers and provide bonding between them without preventing moisture vapor transmission. Advantageously the bonding layer is applied by meltblowing, for example, an amorphous polyolefin such as REXTAC® 2730 or 2330 available from Huntsman Corporation, Salt Lake City, Utah. The meltblown layer when applied at low weights, for example, less than 10 gsm, advantageously less than 5 gsm, is breathable and cost effective. Other examples include Huls Vestoplast® 703, 704 and 508 from Huls AG of Marl, Germany and National Starch NS 5610 from National Starch Chemical Company of Bridgewater, N.J., and the elastomeric compositions described above.

Whether bonded with or without the separately applied bonding layer, the bond strength between the facing and the film as measured by the above described laminate peel test, will desirably exceed the peel strength between the hook facing and the complementary hook as measured by the above described hook peel test, so as to prevent undesired delamination. Advantageously, the difference is at least about 100 g. In addition, for many applications and particularly as a backing for a personal care article such as a diaper, for example, the composite will have a hydrohead as measured by the above described hydrohead test, of at least about 50 mbar of water and advantageously at least about 90 mbar. Especially when used as a backing for disposable personal care products, the composite will have a moisture vapor transmission rate of at least about 100 g/m$^2$/24 hours and advantageously at least about 800 g/m$^2$/24 hours. For these applications, a hook peel strength will desirably exceed 100 g and a hook shear strength, as measured by the above described hook shear test, will desirably exceed 1500 g.

Figure 2:
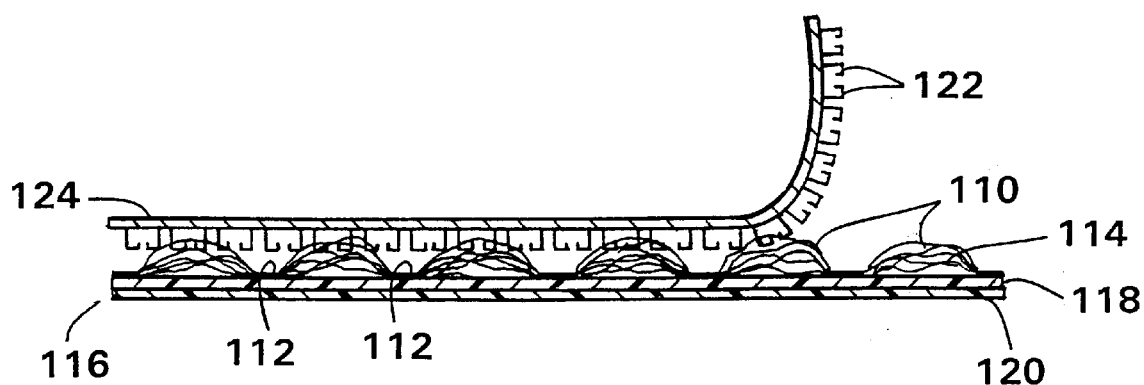
FIG. 2 is a cross-section of one embodiment of a loop fastener material of the present invention.

Referring to FIG. 2, there is shown in cross-section an embodiment of a loop fastener component of the present invention. Loops 110 between bond areas 112 are formed in spunbonded facing layer 114 which is bonded to a coextruded film 116 containing external bonding layer 118 and base layer 120 at each of the prebond points coinciding with a bond laminate area 112. As shown, loop areas 110 are comprised of unbonded filaments or fibers available to entangle hook members 122 of complementary hook member 124. As shown, the hook and loop layers are partially separated for clarity.

Figure 3:
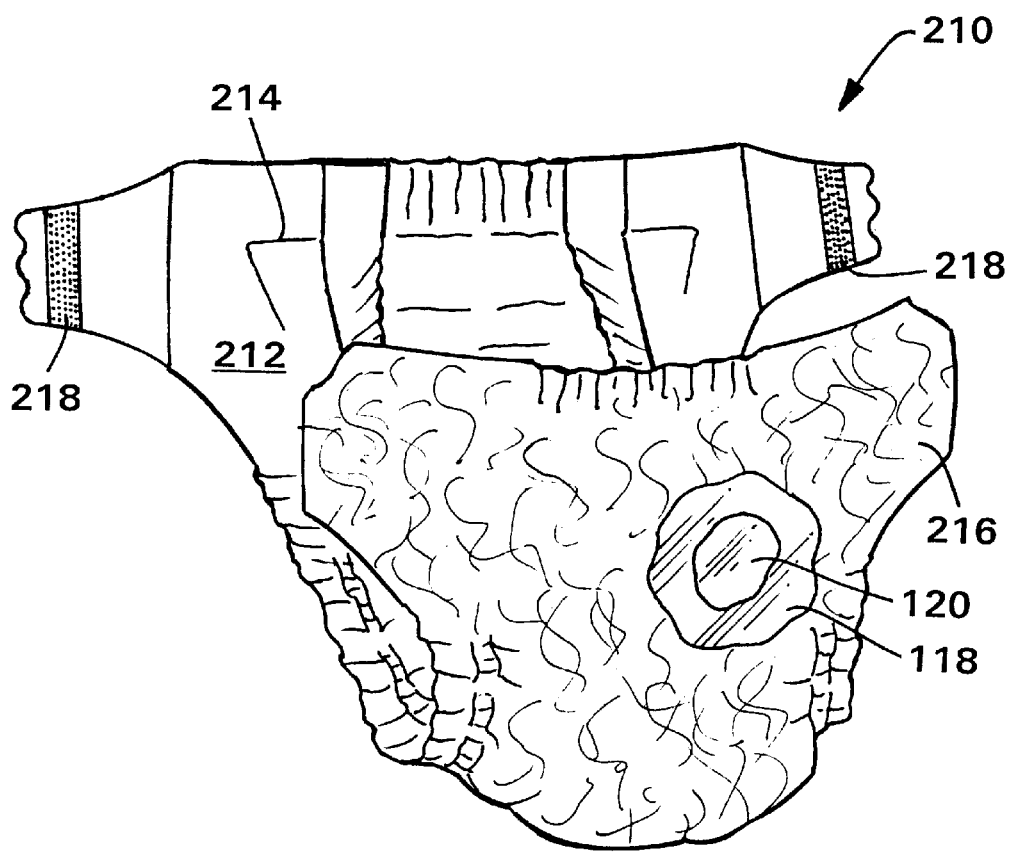
FIG. 3 is an illustration of a loop fastener material of the present invention in use as a backing component of a personal care product.

Referring to FIG. 3, an example of the loop fastener component of the present invention in the form of a backing material for a disposable personal care diaper product is shown. Diaper 210 comprises liner 212, absorbent 214 and backing 216. As is generally known, the liner 212 permits urine to pass through and be absorbed by absorbent 214 while the backing 216 (shown partially broken away showing layers 118 and 120 (FIG. 2) for clarity) is impervious to urine to help avoid leakage. In this case the entire backing is formed from a loop fastener material of the present invention, and as described in connection with FIG. 2, with the nonwoven loops on the outside. This provides an essentially infinite degree of adjustment when combined with hook fastener elements 218. In use, the hook elements 218 can be pulled to a snug fit and fastened anywhere on the backing 216. Furthermore, if adjustment in the fit is desired, the hook elements 218 may be simply peeled away and repositioned anywhere on the backing 216. In advantageous embodiments, the backing is pervious to moisture vapor for increased comfort and dryness.

Figure 4:
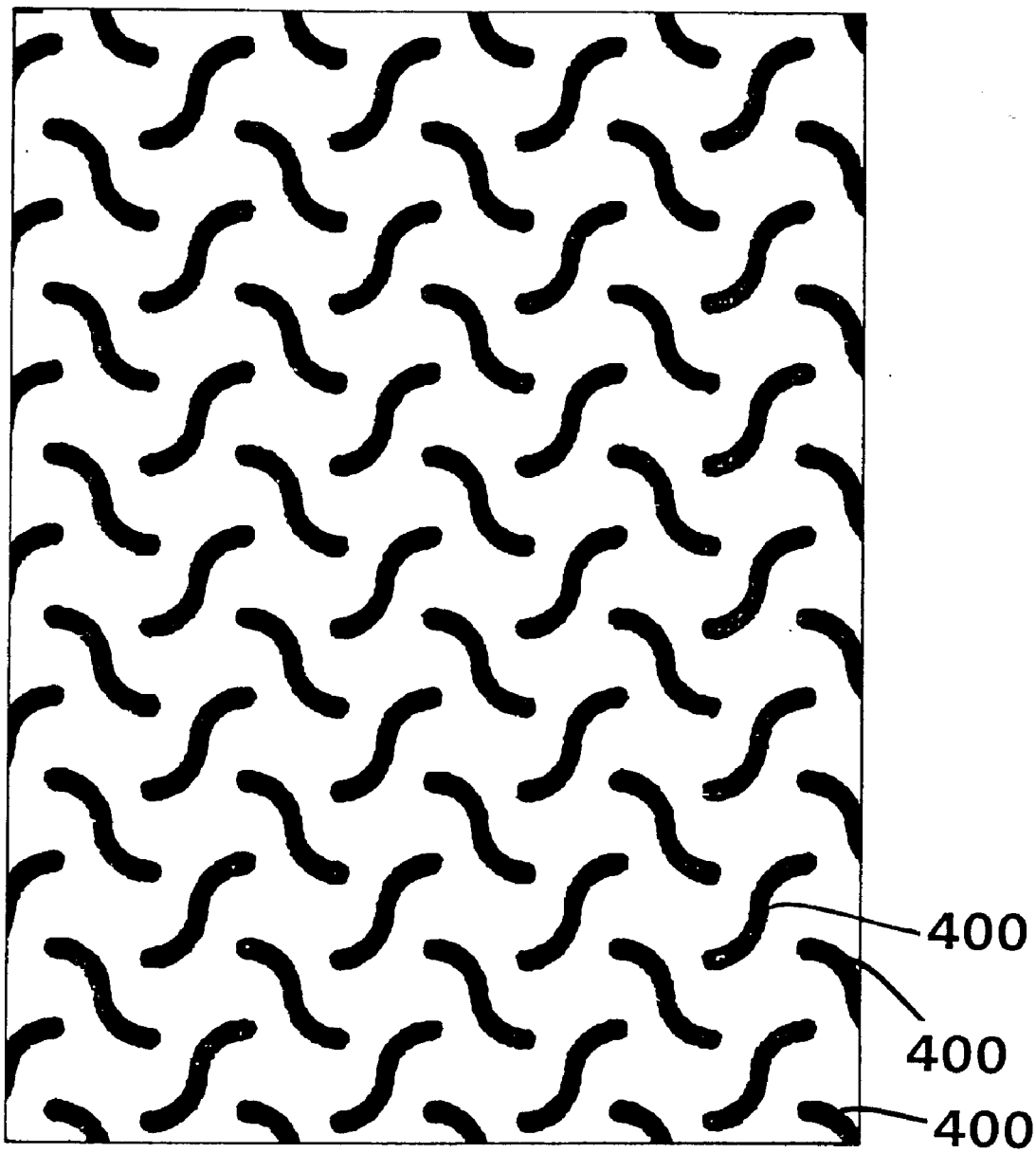
FIG. 4 is an illustration of one bond pattern useful in accordance with the present invention.
Figure 5:
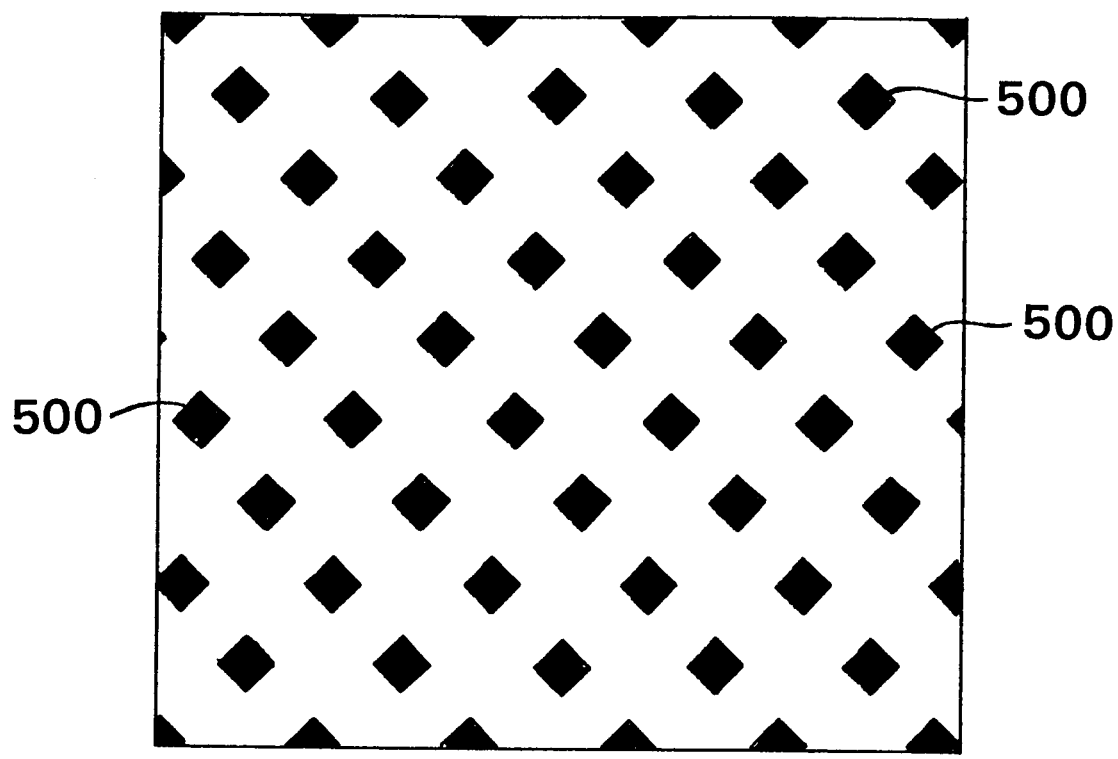
FIG. 5 is an illustration of a second bond pattern useful in accordance with the present invention.

FIGS. 4 and 5 illustrate representative prebond patterns useful in accordance with the prebonded nonwoven component of the composite of the present invention. FIG. 4 shows "S-weave" as described above with prebond areas 400, and FIG. 5 shows "expanded Hansen-Pennings" as described above with bond areas 500.

Figure 6:
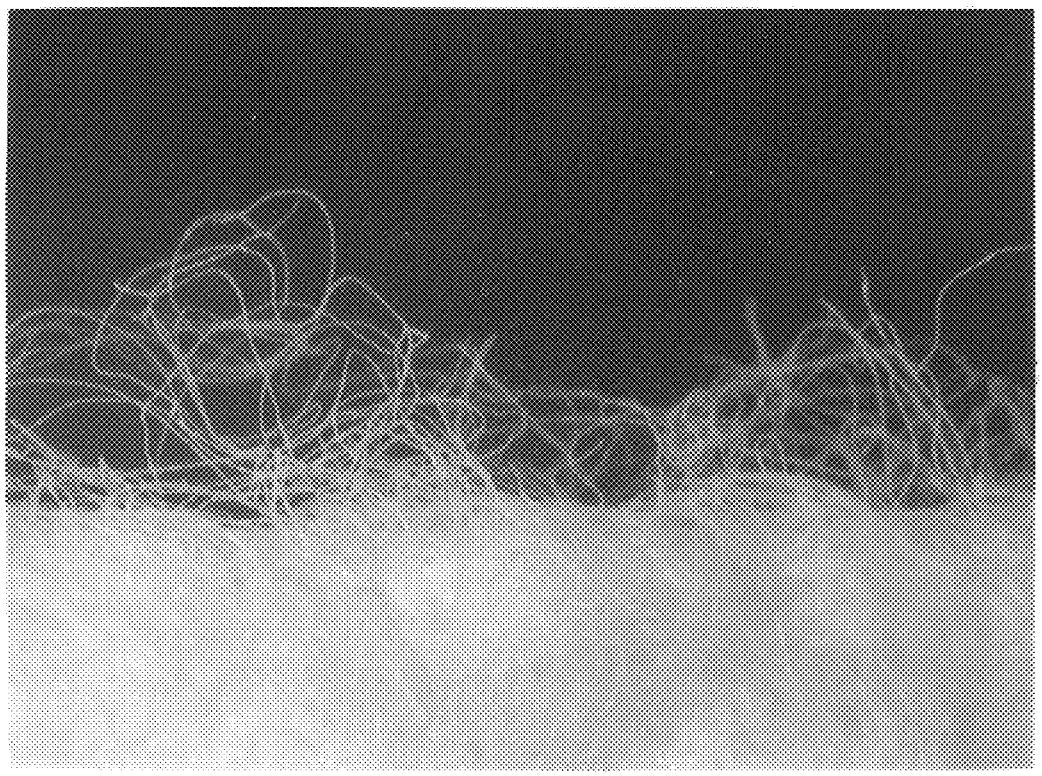
FIG. 6 is a photograph taken at a magnification of about 20× showing a composite material in accordance with the invention after hook peel testing and folded over an edge to expose loose filaments.
Figure 7:
FIG. 7 is a photograph like that of FIG. 6 of a different composite material in accordance with the invention.

FIGS. 6 and 7 are edge view photographs of composite materials in accordance with the invention with an "S-weave" prebond pattern (FIG. 7) and with an EHP prebond pattern (FIG. 6) after hook peel testing. As shown, the EHP comparative material, while, as discussed, having good performance from a hook peel standpoint, had a higher degree of filaments pulled out of the nonwoven as compared with the "S-weave" composite material of the present invention. Both photos were taken at a magnification of about 20× and while the samples were folded over a straight edge to expose loose filaments.

EXAMPLES

For the following examples, a procedure as shown in FIG. 1 was used to form a loop fastener component, except as otherwise indicated.

EXAMPLE 1

For this example the facing material was a spunbond fabric of 2.0 denier filaments made from a copolymer of propylene with 3.5% ethylene (Union Carbide 6D43 available from Union Carbide Corporation of Danbury, Connecticut) and having a basis weight of about 0.7 osy (about 24 gsm) having been bonded with an Expanded Hansen Pennings pattern (with a bond density of 100 pins/in and 16.8% actual measured bond area). The film used was monolayer blown 45% by weight LLDPE (Dowlex® NG 3347A, 0.917 glcc density, melt index at 190° C. of 2.3 g/10 min. available from Dow Chemical Co. of Midland, Mich.), 50% Supercoat™, a ground, stearic acid coated CaCO₃ (available from English China Clay), and 5% LDPE (Dow 6401 0.922 g/cc, melt index at 190° C. of 2.0 g/10 min. available from Dow Chemical) having an initial gauge of 1.5 mil. This film is described in detail in coassigned U.S. Ser. No. 773,826 filed Dec. 27, 1996 in the names of Haffner et al., which is incorporated in its entirety by reference. An amorphous polyolefin (Rextac 2715, available from Huntsman Corporation of Salt Lake City, Utah) meltblown bonding layer was applied to the spunbond surface at a basis weight of about 3.5 gsm at a melt temperature of 177° C. and separation distance of about 10 cm. Prior to laminating the film was stretched at 4× on a machine direction orienter to render it microporous at a temperature of 71° C. The film was maintained under tension as it was nipped between a smooth rubber (Shore A 40) roll and smooth steel roll to the spunbond at 15 PLI. After lamination, the composite was allowed to relax by annealing it at a temperature of 116° C. while allowing it to retract 10% (annealing roll speed: 100 fpm, winder: 90 fpm) and then cooling it with air stream at 15° C. The resulting laminate had a basis weight of 49 gsm, unsupported hydrohead of 220 mbar, and water vapor transmission rate (WVTR) of 1326 g/m²/24 hours. When tested with a complementary hook member using Velcro 858 hook fastener component from Velcro International of Manchester, N.H., a hook peel strength of 402 g and hook shear strength of 2919 g was obtained, based on an average of 10 tests.

EXAMPLE 2

For this example the facing material was a spunbond fabric of about 2.0 denier filaments made from a copolymer of propylene with 3.5% ethylene (Union Carbide 6D43 from Union Carbide Corporation) and having a basis weight of about 0.65 osy (about 20 gsm) having been bonded with an "S-weave" pattern with a bond density of 111 pins/in and 17.7% actual measured bond area) as described in copending and coassigned U.S. Pat. application Ser. No. 929,808 filed Sep. 15, 1997 in the names of McCormack et al. and entitled "Nonwoven Bonding Patterns Producing Fabrics with Improved Strength and Abrasion Resistance" (Attorney Docket No. 13324), the entire contents of which is incorporated herein by reference. The film was monolayer cast 47% by weight LLDPE (Dowlex® NG 3310, 0.918 g/cc density, melt index at 190° C. of 3.5/10 min. available from Dow Chemical Co.), 48% Supercoat™, a ground, stearc acid coated CaCO₃ (available from English China Clay) and 5% LDPE (Dow 4012, 0.916 g/cc density, melt index at 190° C. of 12.0 g/10 min. available from Dow Chemical Co.) (case:12,441 filed December 1996) having an initial gauge of 1.5 mil. An amorphous polyolefin (Rextac 2730 from Huntsman Corporation, Salt Lake City, Utah) meltblown bonding layer was applied to the spunbond surface at a basis weight of about 3.0 gsm, and melt temperature of 177° C. and separation distance of about 11.5 cm. Prior to laminating the film was stretched at 4× on a machine direction orienter to render it microporous at a temperature of 71° C. The film was maintained under tension as it was nipped between a smooth rubber (Shore A 40) roll and smooth steel roll to the spunbond at 15 PLI. After lamination, the composite was allowed to relax by annealing it at a temperature of 110° C. while allowing it to retract as laminate 10% (annealing roll speed: 300 fpm, winder: 270 ft/min) and then cooling it with air stream at 15° C. The resulting laminate had a basis weight of 51 gsm, unsupported hydrohead of 170 mbar, and water vapor transmission rate (MVTR) of 2429 g/m²/24 hours. When tested with a complementary hook member using Velcro 51-1003 hook fastener component, a hook peel strength of 174 g and hook shear strength of 2960 g was obtained based on an average of 10 tests.

EXAMPLE 3

For this example, the film used was a cast coextruded "AB" film having a base layer of 45% LLDPE (Dowlex® NG 3310, 0.918 g/cc density, melt index at 190° C. of 3.59/10 min. available from Dow Chemical Co.), 50% Supercoat™, a ground, stearic acid coated CaCO₃ (available from English China Clay), and 5% LDPE (Dow 4012, 0.916 g/cc density, melt index at 190° C. of 12.0 g/10 min. available from Dow Chemical Co.) and a bonding layer on one side of 60% Supercoat™ CaCO₃, 20% amorphous propene-rich polyalphaolefin ("APAO"), (Huls Vestoplast®, 0.865 g/cc density, melt viscosity at 190° C. of 125,000 mPa according to DIN 53 019, available from Huls America, Inc. of Somerset, N.J.) and 20% elastomeric polyethylene (Dow Affinity® EG8200 constrained geometry catalyzed, density 0.87 g/cc, melt index at 190° C. of 5.0 g/10 min, available from Dow Chemical Co.). The base layer constituted 90% by weight, and the bonding layer 10% by weight. Stretching of the film included a preheating step at 50° C., stretching in a single zone 3.8× in the machine direction at 60° C. and annealing at 93° C. The total basis weight of the coextruded film was 58 gsm (about 1.5 mil). This coextruded film was successfully bonded at 204 ft/min (62 m/min) without a separate meltblown bonding layer to the facing layer of Example 2 using a pressure of 15 PLI Shore A 40 rubber/smooth steel nip at 93° C. The laminate was allowed to relax 10% (nip speed: 204 ft/min, winder speed: 180 ft/min). The resulting laminate had a basis weight of 44 gsm, hydrohead of 60 mbar, and MVTR of 423 $g/m^2/24$ hours. When tested with the complementary hook member of Example 2, Velcro 51-1003, a hook peel strength of 238 g and hook shear strength of 3141 g was obtained, based on an average of 10 tests.

For comparison, samples of conventional nonwoven/film laminate diaper backings were tested with the same hook components used in the preceding examples. The following results were obtained: Kimberly-Clark Corporation's Huggies® Ultratrim™ 1996 commercial product nonwoven-film laminate outercover (polypropylene 2.5 denier spunbond bonded with wireweave pattern: 302 pins/in2, 18% bond area) when tested with Velcro hook 858, a hook peel of 29 g and a hook shear of 171 g were obtained on an average of 10 tests. With the Velcro 51-1003 hook, a hook peel of 71 g and a hook shear of 589 g were obtained on an average of 10 tests. It has been determined with consumer use tests that a hook peel of at least about 100 g and hook shear of at least about 1500 g is desired for primary fastening of the product for active toddlers.

Those of skill in this art will recognize that the invention is subject to many variations, modifications and equivalents within the scope of the foregoing description. It is intended that all such modifications, variations and equivalents be included as are embraced by the appended claims. For these purposes equivalents include functional as well as structural and compositional equivalents. For example, a nail and a screw are functional fastener equivalents even though they may be of different structures.

We claim:

1. A breathable, liquid barrier composite comprising:
   a prebonded nonwoven having a pattern of spaced apart bonds with unbonded fibers or filaments between said bonds,
   a film bonded to said nonwoven at locations corresponding to said pattern of spaced apart bonds and otherwise substantially unbonded to said nonwoven,
   wherein said composite has a moisture vapor transmission rate of at least about 100 $g/m^2/24$ hours and a hydrohead value of at least about 50 mbar of water.

2. The composite of claim 1 wherein said spaced apart bonds comprise about 5% to about 30% of said prebonded nonwoven surface area and a bond frequency in the range of from about 50 to about 200 per square inch.

3. The composite of claim 2 wherein said film to nonwoven bonds comprise an amorphous polymer.

4. The composite of claim 3 wherein said film comprises a plurality of layers and said amorphous polymer comprises one of said layers that is in contact with said nonwoven.

5. The composite of claim 3 wherein said amorphous polymer comprises a layer separately applied to said film prior to contact with said nonwoven.

6. The composite of claim 2 wherein said fibers or filaments between said spaced apart bonds are looped, forming engagement areas for a complementary hook fastener component.

7. The composite of claim 6 as a loop component of a hook and loop fastening system wherein said hook peel strength is in the range of from about 100 g to about 800 g.

8. The composite of claim 7 wherein said hook shear strength is in the range of from about 1000 g to about 6000 g.

9. A personal care article comprising the composite of claim 1.

10. A personal care article comprising the composite of claim 8.

11. The personal care article of claim 10 wherein said composite comprises a backing material providing fastenability substantially anywhere on said backing.

12. The personal care article of claim 11 selected from the group consisting of diapers, training pants, incontinent wear and feminine care products.

13. A mechanical fastener comprising hook and loop components wherein the loop component comprises the composite of claim 1.

14. A mechanical fastener comprising hook and loop components wherein the loop component comprises the composite of claim 3.

15. The composite of claim 8 wherein the spaced apart bonds comprise about 10% to about 25% of said prebonded nonwoven surface area.

16. The composite of claim 15 wherein said bond frequency is in the range of from about 75 to about 125 per square inch.

17. The composite of claim 16 having a Martindale abrasion of at least about 3.

18. The composite of claim 17 having a moisture vapor transmission rate of at least about 800 $g/m^2/24$ hours.

* * * * *

UNITED STATES PATENT AND TRADEMARK OFFICE
CERTIFICATE OF CORRECTION

PATENT NO. : 5,997,981

DATED : December 7, 1999

INVENTOR(S) : Ann L. McCormack et al.

Page 1 of 2

It is certified that error appears in the above-identified patent and that said Letters Patent is hereby corrected as shown below:

Column 5, Line 47, "cydes" should read --cycles--

Column 8, Line 42, "Dowlexe" should read -- Dowlex® --

Column 8, Line 45, "up to" should read -- at least --

Column 8, Line 48, Line 9, "Supercoate" should read -- Supercoat® --

Column 9, Line 27, delete "(Attorney Docket No. 13257)"

Column 9, Lines 29 and 30; delete "(Express Mailing No. RB 879662575US)" and insert -- (published as WO 99/14047) --

Column 9, Line 62, delete "(Attorney Docket No. 13,324)" and substitute -- (published as WO 99/14415) --

Column 9, Lines 65 and 66, delete "(Express Mailing No. EM 331625424US)"

Column 11, Lines 47 and 48, delete "U.S. Serial No. 773,826 filed 27-" and insert -- published WO 98/29481--

Column 11, Line 48, delete "December-1996"

Column 11, Line 56, delete "at"

Column 11, Line 62, after "with" insert -- an --

Column 12, Line 2, "was" should read -- were --

Column 12, Lines 17 and 18, delete "(Attorney Docket No. 13324)"

Column 12, Line 21, "stearc" should read -- stearic --

Column 12, Line 26, delete "(case: 12,441 filed 12/96)"

UNITED STATES PATENT AND TRADEMARK OFFICE
CERTIFICATE OF CORRECTION

PATENT NO.  : 5,997,981
DATED       : December 7, 1999
INVENTOR(S) : Ann L. McCormack et al.

It is certified that error appears in the above-identified patent and that said Letters Patent is hereby corrected as shown below:

Column 12, Line 32, delete "at"

Column 12, Line 40, after "with", insert -- an --

Column 12, Line 45, "was" should read -- were --

Column 12, Line 52, "3.59/10" should read -- 3.5g/10 --

Column 13, Line 12, "was" should read -- were --

Signed and Sealed this

Second Day of January, 2001

Attest:

Attesting Officer

Q. TODD DICKINSON
Commissioner of Patents and Trademarks